(12) United States Patent
Sano et al.

(10) Patent No.: US 7,648,526 B2
(45) Date of Patent: Jan. 19, 2010

(54) EXTENDABLE SOFT STENT WITH EXCELLENT FOLLOW-UP CAPABILITY TO BLOOD VESSEL

(75) Inventors: Yoshihiko Sano, Osaka (JP); Yuji Tanaka, Osaka (JP)

(73) Assignee: Nipro Corporation, Osaka (JP)

( * ) Notice: Subject to any disclaimer, the term of this patent is extended or adjusted under 35 U.S.C. 154(b) by 651 days.

(21) Appl. No.: 10/554,725

(22) PCT Filed: Apr. 27, 2004

(86) PCT No.: PCT/JP2004/006057

§ 371 (c)(1),
(2), (4) Date: Oct. 27, 2005

(87) PCT Pub. No.: WO2004/096340

PCT Pub. Date: Nov. 11, 2004

(65) Prior Publication Data

US 2007/0005123 A1     Jan. 4, 2007

(30) Foreign Application Priority Data

Apr. 30, 2003 (JP) ............................. 2003-125827
May 20, 2003 (JP) ............................. 2003-141381
Aug. 11, 2003 (JP) ............................. 2003-291384

(51) Int. Cl.
*A61F 2/06* (2006.01)
(52) U.S. Cl. .................................................. 623/1.17
(58) Field of Classification Search ................ 623/1.15, 623/1.17

See application file for complete search history.

(56) References Cited

U.S. PATENT DOCUMENTS

| 4,733,665 | A | 3/1988 | Palmaz |
| 6,497,723 | B1 | 12/2002 | Starck et al. |
| 6,540,775 | B1 | 4/2003 | Fishell et al. |
| 7,357,813 | B2 * | 4/2008 | Burgermeister ............ 623/1.17 |
| 2002/0123797 | A1 | 9/2002 | Majercak |
| 2003/0055485 | A1 | 3/2003 | Lee et al. |

FOREIGN PATENT DOCUMENTS

| EP | 0 876 806 A1 | 11/1998 |
| JP | 62-231657 A | 10/1987 |
| JP | 6-181993 A | 7/1994 |
| JP | 8-155035 A | 6/1996 |

(Continued)

*Primary Examiner*—Anhtuan T Nguyen
*Assistant Examiner*—Eric Blatt
(74) *Attorney, Agent, or Firm*—Birch, Stewart, Kolasch & Birch, LLP

(57) ABSTRACT

The stent of the present invention is a tubular member comprising annular members 1 arranged in a longitudinal direction thereof for keeping a body lumen open, and one or more connecting elements 2 for connecting longitudinally adjoining two annular members 1, 1 with one another. Each annular member 1 comprises first annular member elements 11 and second annular member elements 12 which are alternately jointed together in the circumferential direction of the annular member 1. The annular members 1 are expandable in the radial direction thereof. The stent is flexible and excellent in trackability to lumens, thus making it possible to allow the stent to pass through the three-dimensionally meandering lumens. The stent is substantially free from shortening and makes it possible to provide the stent with a lateral hole.

13 Claims, 16 Drawing Sheets

FOREIGN PATENT DOCUMENTS

| | | |
|---|---|---|
| JP | 10-503676 A | 4/1998 |
| JP | 11-505441 A | 5/1999 |
| JP | 2002-17869 A | 1/2002 |
| JP | 2002-530146 A | 9/2002 |
| JP | 2003-24451 A | 1/2003 |
| WO | WO-96/03092 A1 | 2/1996 |
| WO | WO-96/26689 A1 | 9/1996 |
| WO | WO-99/12495 A1 | 3/1999 |
| WO | WO-00/30563 A1 | 6/2000 |
| WO | WO-03/024363 A1 | 3/2003 |

* cited by examiner (a)                (b)

EXTENDABLE SOFT STENT WITH EXCELLENT FOLLOW-UP CAPABILITY TO BLOOD VESSEL

TECHNICAL FIELD

The present invention relates to a stent that is implanted in a human body to maintain a diameter of a body lumen such as blood vessels.

BACKGROUND ART

So far, stents have been used to expand a diameter of the body lumen such as the blood vessel and keep it to the expanded luminal diameter. The stent may be expanded by various methods such as balloon dilation, self-expansion using a shape memory material, mechanical expansion, or the like. The most widely used method is the balloon dilation. In the balloon dilation, a stent is introduced into a desired site in the body together with a balloon catheter, expanded by inflation of balloon to dilate a diameter of the lumen, and retained at the dilated site even after removing the deflated balloon from the site. The stent generally comprises luminal diameter-holding portions for dilating and holding the diameter of the lumen such as blood vessel, and joint portions for connecting the luminal diameter-holding portions in the longitudinal direction of the stent, and the stent is adapted to keep its expanded shape after expansion.

Proposed stents comprising luminal diameter-holding portions and joint portions include, for example, a stent comprising plural cylindrical components which are separately expandable in the radial direction thereof and are connected to one another so as to align on a common axis (JP-H06-181993 A); a stent comprising a tubular member expandable in the radial direction, the tubular member being constituted by a plurality of elongated members intersecting with one another (JP S62-231657 A); a stent comprising at least two unitary wire-like circular members each bent to form a plurality of substantially straight, non-overlapping segments connected at axial bends; the at least two circular members having at least one pair of aligned axial bends; and the at least two circular members connected by at least one substantially rigid joint at least one pair of aligned axial bends (JP H08-155035 A); a stent formed of a tube having a patterned shape which has first and second meander patterns having axes extending in first and second directions (JP H10-503676 A); and a stent with an open structure comprising a plurality of open cylindrical segments, each segment being defined by an interconnected struts, the segment being interconnected at end portions thereof by a plurality of diagonal interconnecting elements (JP H11-505441 A).

These stents of the prior art have been improved to some extent, but they still put a load on the lumen such as the blood vessel in the vicinity of edges of the expanded stent, resulting in obstruction or stenosis of the lumen. Further, it can not be said that these stents have sufficient flexibility, and thus it is often difficult to insert the stent into the objective site if the lumen has a three-dimensionally meandering course. In addition, the stents may cause wounds in the blood vessel during insertion into the objective site. If there is a branched blood vessel at the inflated position, it is hardly difficult to form a lateral hole in the placed stent. Further, the stents have such a problem that the length of the stent is shortened by expansion, i.e., so-called shortening.

DISCLOSURE OF INVENTION

In view of the above circumstances, the present invention has been made to provide a flexible stent with excellent expandability, which is excellent in trackability to lumens (thus making it possible to pass through the three-dimensionally meandering lumens), substantially free from shortening, and enables to provide the stent with a lateral hole.

A stent according to the present invention (i.e., first invention) comprises a plurality of annular members which are radially expandable and are aligned in a longitudinal direction thereof, and one or more connecting elements for connecting the adjoining two annular members with one another in the longitudinal direction thereof, said annular members each comprising first annular member elements and second annular member elements which are alternately interconnected in the circumferential direction of the stent, said stent, when unfolded onto a plane, possessing such configurations that said first annular member element includes three longitudinally extending parallel linear segments of first, second and third linear segments, the second linear segment and third linear segment being equal in length, while the first linear segment having a length longer than that of the second and third linear segments, said first linear segment and second linear segment being connected by an arched segment protruded leftwards (towards the proximal end of the stent), while said second linear segment and third linear segment being connected by an arched segment protruded rightward (towards a distal end of the stent), said second annular member elements each including three longitudinally extending, parallel linear segments of first, second and third linear segments, said second linear segment and third linear segment being equal in length, while said first linear segment having a length longer than that of said second and third linear segments, said first linear segment and second linear segment being connected by an arched segment protruded rightward (towards a distal end of the stent), while said second linear segment and third linear segment being connected by an arched segment protruded leftwards (towards the proximal end of the stent), about the first and second annular member elements, the second annular member element and the first annular member element located above the second annular member element being connected by an arched segment, which is convex leftwards (towards the proximal end of the stent) and located between the first linear segment of the second annular member element and the third linear segment of the first annular member element, while the second annular member element and the first annular member element located below the second annular member element being connected by an arched segment, which is convex rightward (towards the distal end of the stent) and located between the third linear segment of the second annular member element and the first linear segment of the first annular member element, the adjoining two annular members being connected by the connecting elements at corresponding arched segments of the first annular member element and the second annular member elements.

The term "corresponding arched segments" here means twin arched segments that connect the first linear segment and the second linear segment, or twin arched segments that connect the second linear segment and the third linear segment, or twin arched segments that connect the third linear segment and the first linear segment. In order to substantially eliminate change in length of the stent when expanding the stent, it is preferred to construct the stent such that the first linear segment is longer than the second linear segment and third linear segment, and that the adjoining annular members are connected at portions of the arched segments that connect the second linear segment and third linear segment of the respective annular members. Further, it is preferred that the ratio between a distance from a radially halving line of the annular member to a top of the arched segment that connects the second linear segment and the third linear segment of the first annular member elements, and a distance from a radially halving line of the annular member to a top of the arched segment that connects the first linear segment and the second linear segment of the second annular member elements are set to a value within the range of 1:2-7:8. Although the degree of expansion of the stent and effects of the connecting elements should be taken into account, the expanded stent has a tendency to increase the length thereof when the ratio between the distances is less than 1:2, but it has a tendency to decrease the length when the ratio of that distance exceeds 7:8. Further, the adjoining annular members may be out of phase with each other. In particular, it is preferred that the adjoining two annular members are out of phase with each other by a half wavelength and are connected by the connecting elements in the same longitudinal straight lines.

The connecting element may have the shape of a linear or curved line. However, it is preferred that the connecting element has a waveform having one or more wave peaks, from the viewpoint of flexibility and formation of lateral holes. It is preferred to provide two to six pieces of the connecting elements at regular intervals as occasion demands.

The arched segments on the proximal side of the proximal annular member and those on the distal side of the distal annular member may be aligned. The linear segments of the first annular member element and the linear segments of the second annular member element may be arranged circumferentially at regular intervals. The interval between the first linear segment and the second linear segment may be equal to the interval between the third linear segment and the first linear segment, but smaller than that between the second linear segment and the third linear segment.

As a material for the stent, it is possible to use stainless steel, tungsten, tantalum, nickel-titanium alloys, and the like.

According to a second aspect of the present invention (or a second invention), there is provided a stent comprising radially expandable annular members comprising wavelike elements each having an M-shaped waveform and being joined together in the circumferential direction of the annular member, and one or more connecting elements which connect said annular members in the longitudinal direction of the stent, said annular members being aligned in the longitudinal direction of the stent, adjoining two annular members being connected with said connecting elements by connecting a top of a small mountain of a trough element in at least one wavelike element of one annular member with a bottom of a small trough of a mountain element in at least one wavelike element of the other annular member.

In the present invention, the term "mountain" means a waved section that is convex toward the distal end of the stent (or concave toward the proximal end of the stent), while the term "trough" means a waved section that is concave toward the distal end of the stent (or convex toward the proximal end of the stent). The term "wavelike element with an M-shaped waveform" means a wavelike element comprising a combination of a mountain element of the wave having a trough between two mountains (M-shape) and a trough element of the wave having a mountain between two troughs (reversed M-shape). The wavelike element is never limited to a particular shape, provided that the wavelike element has one trough (or mountain) between two mountains (or troughs). Further, four line segments (ridgelines of the mountains and troughs) which constitute each M-shaped wavelike element, take the form of a substantially sinusoidal wave, but they do not necessarily take the form of the substantially sinusoidal wave. They may be in the form of a linear or parallel line. In that case, the line segment including a connecting point between the M-shaped element and the reversed M-shaped element, corresponds to the first linear segment of the first annular member element or second annular member element, and a length of the line segment is longer than the two line segments forming the mountain or trough (corresponding to the second linear segment or third linear segment of the first annular member element or second annular member element). However, the two line segments forming the mountain or trough are not necessarily required tot have the same length, and the line segment of the middle position (corresponding to the second linear segment) may be shorter than the line segment of the lower position (corresponding to the third linear segment).

Here, it is preferred that the mountain positioned in the middle portion of two troughs in the wavelike element is protruded on the side of the mountain in the wave element since the mountain protruded on the side of the trough causes elongation of the stent when expanding the stent. Further, the protruded length of the mountain is preferably ½ to ⅞ of the wave height of the wavelike element. In addition, the adjoining two annular members may be out of phase with each other. In that case, it is preferred that the adjoining two annular members are out of phase with each other by a half wavelength of the wavelike element and are connected by the connecting elements in the same longitudinal straight lines.

The connecting element may take the form of a linear line or a curved line. It is preferred to provide two to six connecting elements at regular intervals between the adjoining two annular members as occasion demands.

It would be understood that the wavelike element in the second invention, in which the four line segments constituting the M-shaped wavelike element are linear and in parallel with each other, correspond to the wavelike element of the first present invention, in which the first linear segment is longer than the second and third linear segments and in which the adjoining two annular members are connected at the arched segment that connects the second linear segment and the third linear segment.

According to the present invention, it is possible to expect the following effects: (1) the whole stent is excellent in trackability to lumens since the stent as a whole possesses flexibility to bending because of the fact that the annular members forming the tubular wall of the stent are composed of repeated wavelike patterns, and it is easy to form a lateral hole; (2) the adjoining two annular members are connected by the connecting elements at the arched segment that connects the second linear segment and the third linear segment with small wave amplitudes of the wave pattern, there is substantially no change in length of the stent when expanding the stent, provided that the ratio between the distance from a radially halving line of the annular member to the top of the arched segment that connects the second linear segment and the third linear segment of the first annular member element, and the distance from a radially halving line of the annular member to the top of the arched segment that connects the first linear segment and the second linear segment of the second annular member element has been set to a value falling within the range of from 1:2 to 7:8. (3) since the adjoining two annular members are connected by the connecting members at the tops of the arched segments that are the mountains of the wavelike pattern, the tops of the arched segments are free from curvature deformation at the time of expansion of the stent and are reduced in curvature deformation at the time of bending of the stent, thus making it possible to minimize the damage of the lumens at the time of introduction of the stent into the objective site.

BEST MODE FOR CARRYING OUT THE INVENTION

In the stent defined as above, the ratio between the distance from the radially halving line of the annular member to the top of the arched segment that connects the second linear segment and the third linear segment of the first annular member element, and the distance from the radially halving line of the annular member to the top of the arched segment that connects the first linear segment and the second linear segment of the second annular member element is set to 3:4. At the same time, the adjoining two annular members are out of the phase with one another by a half wavelength of the wavelike element and connected with one another by the connecting elements in the same longitudinal straight lines. The annular member situated at each end of the stent is so designed that the arched segments of each annular member are respectively aligned along the proximal or distal end of the stent.

Embodiment 1 Across the Bottom

Figure 1:
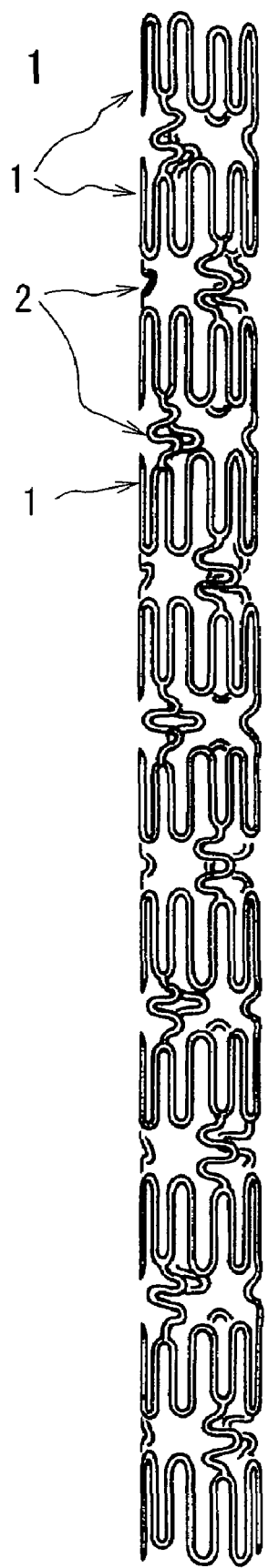
FIG. 1 is an enlarged plan view of a stent according to one embodiment of the present invention.
Figure 2:
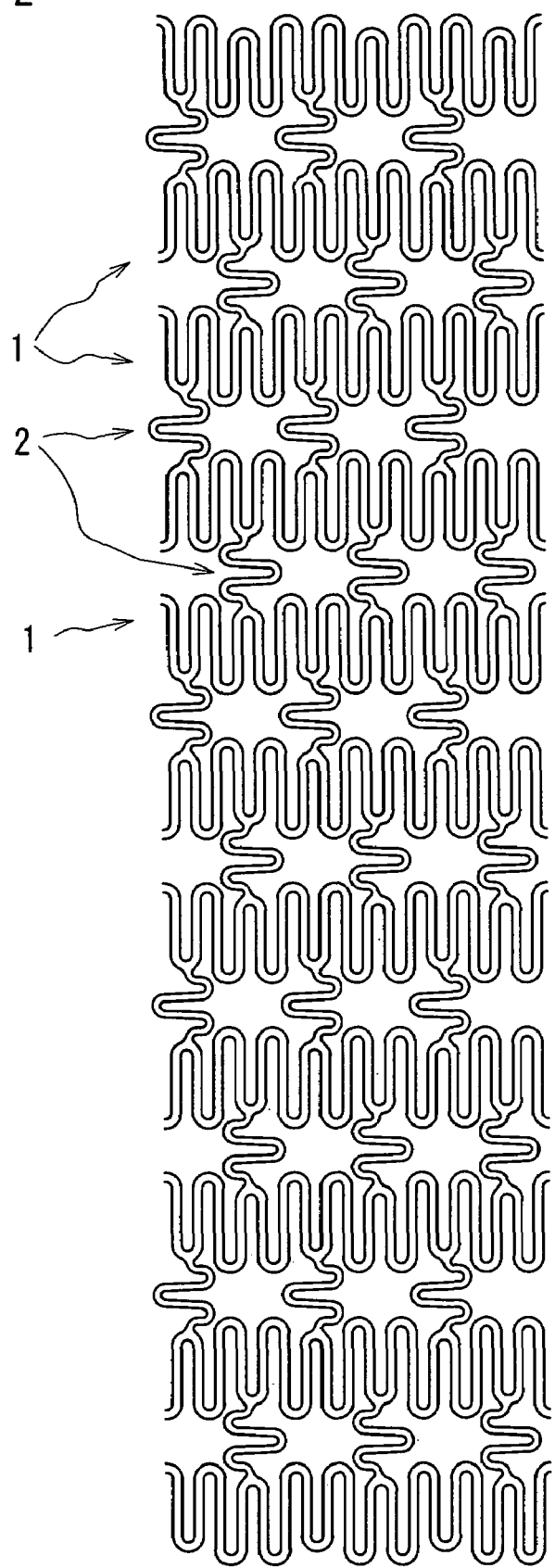
FIG. 2 is a development of the stent shown in FIG. 1.
Figure 3:
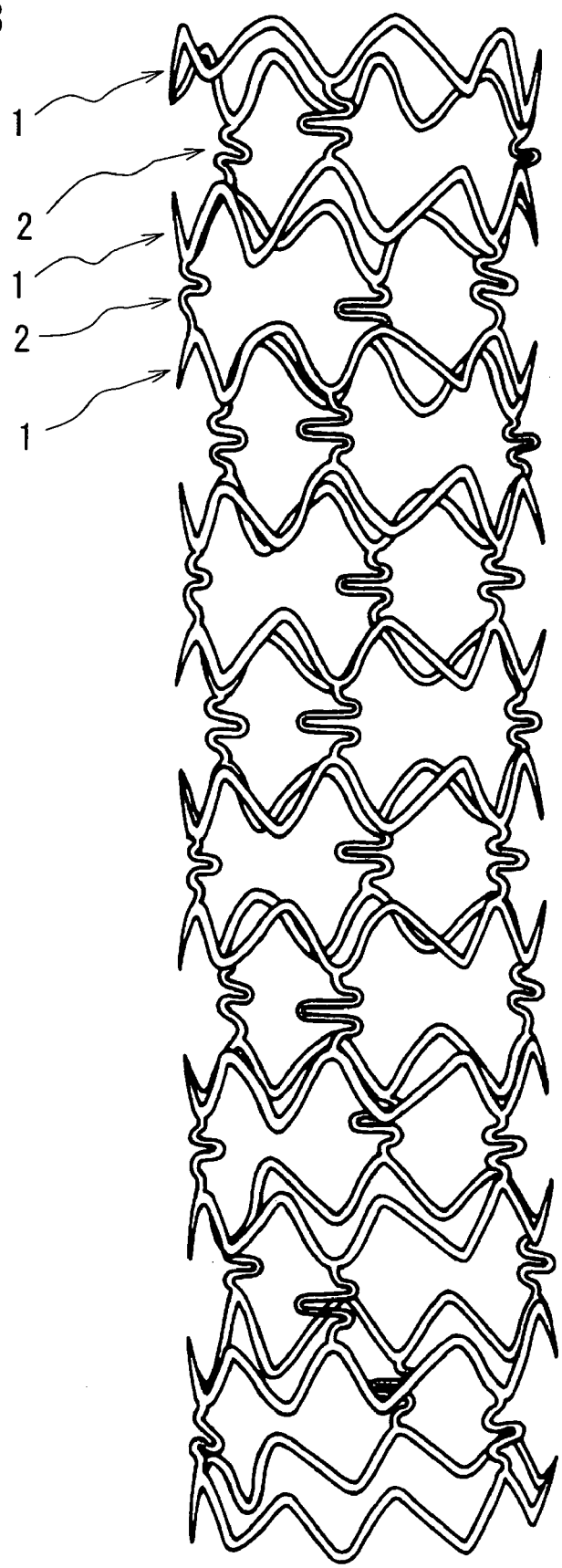
FIG. 3 is an enlarged plan view illustrating an expanded state of the stent shown in FIG. 1.
Figure 4:
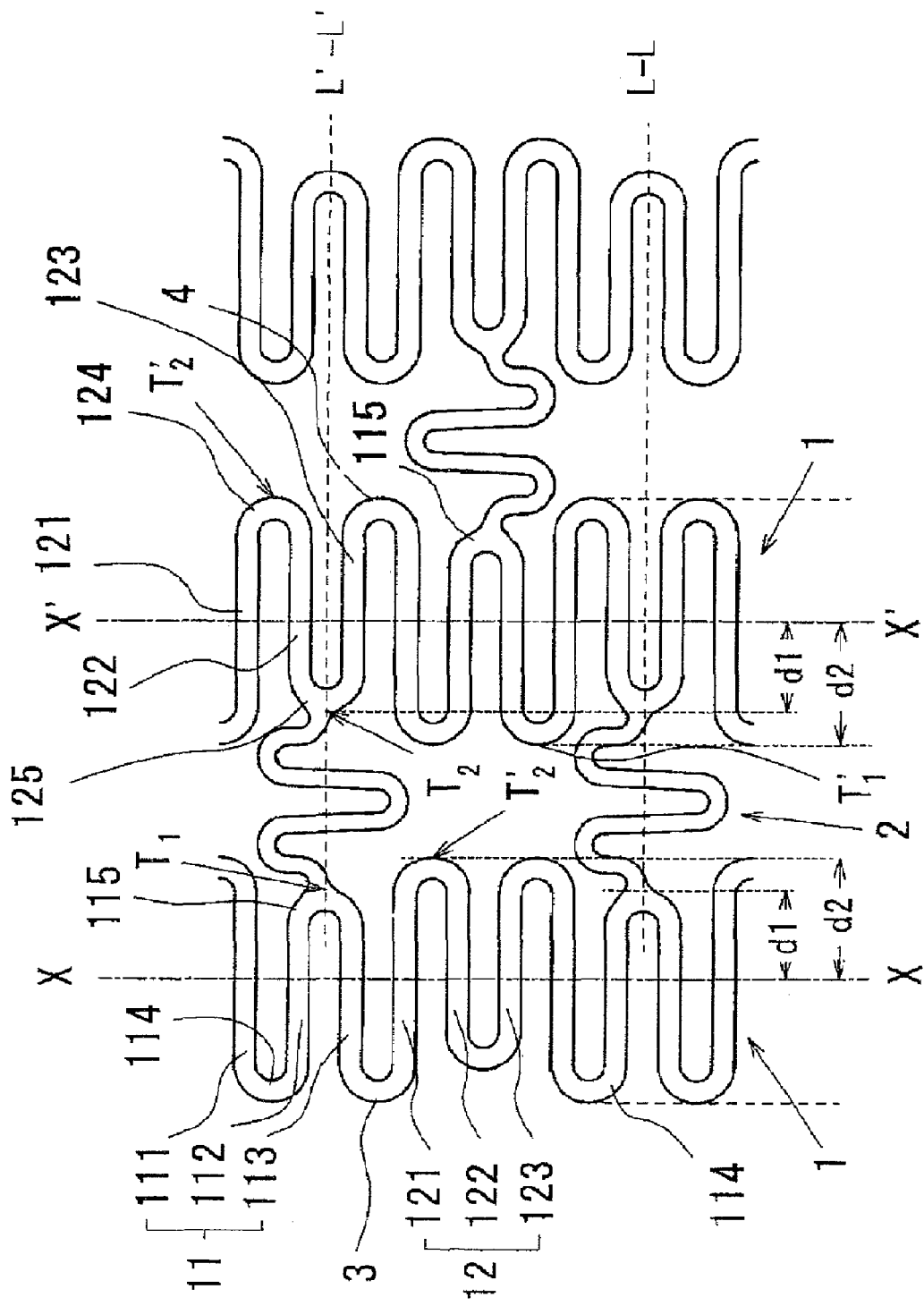
FIG. 4 is a partially enlarged view of FIG. 2.

FIG. 1 is an enlarged plan view of a stent according to one embodiment of the present invention, FIG. 2 is a development of the stent shown in FIG. 1, FIG. 3 is an enlarged plan view illustrating an expanded state of the stent shown in FIG. 1, and FIG. 4 is a partially enlarged view of FIG. 2.

As shown in FIGS. 1 to 3, the stent of embodiment 1 is a tubular member comprising eleven annular members 1 arranged in the longitudinal direction of the stent for keeping a body lumen open, and connecting elements 2 arranged by threes between the longitudinally adjoining two annular members 1, 1 to connect them with one another. Each annular member 1 comprises three pieces of first annular member elements 11 and three pieces of second annular member elements 12, which are alternately interconnected in the circumferential direction to define the annular member, which is expandable in the radial direction.

The first annular member elements 11 and second annular member elements 12 under the conditions that the stent is unfolded onto a plane are continued in the vertical direction as shown in FIGS. 2 and 4. The first annular member element 11 includes three longitudinally extending, parallel linear segments 111, 112, 113 of first, second and third positions. The second linear segment 112 and third linear segment 113 are of the same length, but the first linear segment 111 has a length longer than that of the second and third linear segments. The first linear segment 111 and second linear segment 112 are connected by an arched segment 114 which is convex leftward, while the second linear segment 112 and third linear segment 113 are connected by an arched segment 115 which is convex rightward.

On the other hand, the second annular member element 12 includes three longitudinally extending parallel linear segments 121, 122, 123 of first, second and third linear segments. The second linear segment 122 and third linear segment 121 are of the same length, but the first linear segment 121 has a length longer than that of the second and third linear segments. The first linear segment 121 and second linear segment 122 are connected by an arched segment 124 which is convex rightward, while the second linear segment 122 and third linear segment 123 are connected by an arched segment 125 which is convex leftward.

About the first and second annular member elements 11, 12, the second annular member element 12 and the first annular member element 11 located above the second annular member element 12 is connected by an arched segment 3, which is convex leftwards and located between the first linear segment 121 of the second annular member element 12 and the third linear segment 113 of the first annular member element 11, while the second annular member element 12 and the first annular member element 11 located below the second annular member element 12 is connected by an arched segment 4, which is convex rightward and located between the third linear segment 123 of the second annular member element 12 and the first linear segment 111 of the first annular member element.

Further, a ratio of a distance $d_1$ from a radially halving line X, X' of the annular member to the top $T_1$, $T_2$ of the connected arched segment 115, 125 to a distance $d_2$ from the radially halving line X, X' to the top $T_1'$, $T_2'$ of the unconnected arched segment 124, 114 (i.e., a ratio between a distance $d_1$ from the radially halving line X of the annular member to the top $T_1$ of the arched segment 115, that connects the second linear segment 112 and the third linear segment 113 of the first annular member element 11, and a distance $d_2$ from the radially halving line X of the annular member to the top $T_2'$ of the arched segment 124, that connects the first linear segment 121 and the second linear segment 122 of the second annular member element 12; or a ratio between a distance $d_1$ from the radially halving line X' of the annular member to the top $T_2$ of the arched segment 125, that connects the second linear segment 122 and the third linear segment 123 of the second annular member element 12, and a distance $d_2$ from the radially halving line X' of the annular member to the top $T_1$ of the arched segment 114, that connects the first linear segment 111 and the second linear segment 112 of the first annular member element 11, hereinafter referred to as a "ratio of distances from the radially halving line X to the respective tops of the arched segments") is set to 4:5. The adjoining two annular members 1, 1 are out of phase with each other by a half wavelength of the annular member element, and are interconnected at a part of the arched segment 115, which connects second linear segment 112 and third linear segment 113 of the first annular member element 11 on the left side, and at a part of the arched segment 125, which connects second linear segment 122 and third linear segment 123 of the second annular member element 12 on the right side, in the same longitudinal straight lines (See, for example, longitudinal straight L-L and L'-L' in FIG. 4) by three connecting elements 2 having a configuration as shown in FIG. 5B.

The above stent is flexible enough to respond to bending since the annular members that constitute the stent wall are composed of repeated wavelike patterns, and thus excellent in trackability to lumens. Further, it is easy to provide the stent with a lateral hole. Since the adjoining two annular members are joined together at the arched segments each connecting the second linear segment and the third linear segment with small amplitude of a wavelike pattern and since the ratio between the distance from the radially halving line of the annular member to the top of the arched segment that connects the second linear segment and the third linear segment of the first annular member and the distance from the radially halving line of the annular member to the top of the arched segment that connects the first linear segment and the second linear segment of the second annular member is set to 4:5, there is scarcely any change in length of the stent by expansion of the stent. In addition, the adjoining two annular members are connected at parts of the arched segments, which are the tops of the wavelike patterns, and thus the tops of the wavelike patterns are free from curvature deformation at the time of expansion of the stent and are reduced in curvature deformation at the time of bending of the stent, thus making it possible to minimize damages of blood vessel which may occur at the time of guiding the stent to the site to be applied, Embodiment 2

Figure 6:
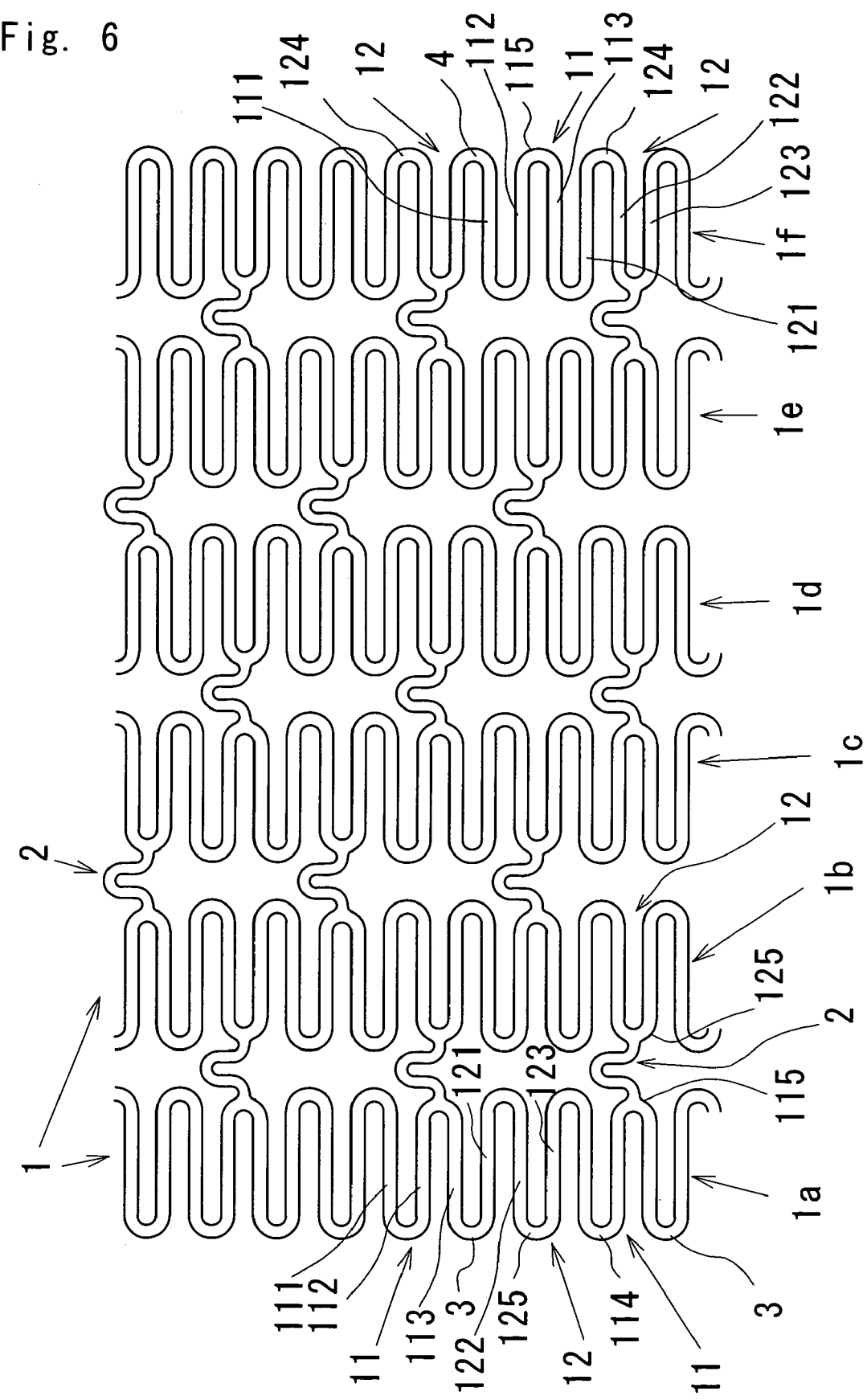
FIG. 6 is a development of a stent according to another embodiment of the present invention.

Embodiment 2 of the present invention will be demonstrated below, making reference to FIG. 6.

Figure 5A:
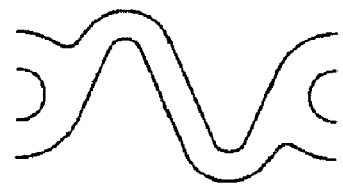
FIG. 5 shows embodiments of the connecting elements in the present invention, illustrating conditions connected with the arched segments.
Figure 5B:
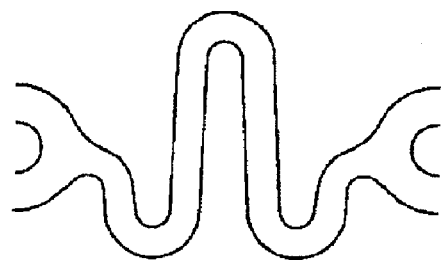
Figure 5C:
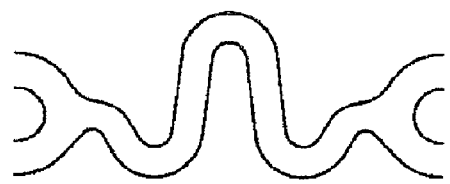
Figure 5D:
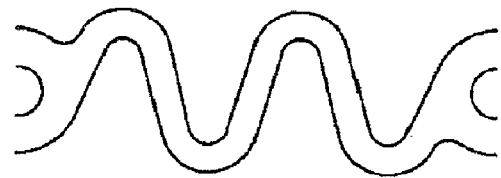
Figure 5E:
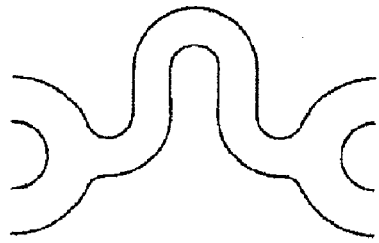

The stent of embodiment 2 is a modification of the stent of embodiment 1, wherein the ratio of distances from the radially halving line to the respective tops of the arched segments is set to 7:8, and the arched segments 125, 114, 3 and arched segments 124, 4, 115 are respectively aligned with one another at the proximal end of the annular member 5 on the proximal side of the stent or at the distal end of the annular member 6 on the distal side of the stent, and the connecting elements 2 are formed into a shape shown in FIG. 5E. As illustrated in FIG. 6, the stent comprises six annular members 1a-1f, which are radially expandable, and the adjoining two annular members 1 are connected to each other by three wavelike connecting elements 2 as shown in FIG. 5E.

The arched segments of the annular members situated at each end of the stent are respectively aligned along the proximal or distal end of the stent. That is, the annular member 1a is designed such that the positions of the arched segments 114 and 3 are aligned with the position of the arched segment 125 by shortening the first linear segments 111, second linear segments 112 and third linear segments 113 of the annular member element 11 and the first linear segments 121 of the second annular member element 12 on the side of the proximal end of the annular member. On the other hand, the annular member 1f is designed such that the positions of the arched segments 124 and 4 are aligned with the position of the arched segments 115 by shortening the first linear segments 111 of the first annular member element 11 and the first linear segments 121, second linear segments 122 and third linear segments 123 of the second annular member element 12 on the side of the distal end of the annular member 1f.

The alignment of the arched segments may be done by lengthening the second linear segments 112 and third linear segments 113 of the first annular member elements 11 of the annular member 1f on the side of the distal end of the stent to align the positions of the arched segments 115 with the positions of the arched segments 124 and 4, while by lengthening the second linear segments 122 and third linear segments 123 of the second annular member elements 12 of the annular member 1a on the side of the proximal end of the stent to align the positions of the arched segments 125 with the positions of the arched segments 114 and 3.

The stent of the above embodiment is excellent in traceability to lumens since the whole stent is flexible enough to respond to bending. Further, it is easy to provide the stent with a lateral hole. In addition, it is possible to avoid damages of the blood vessels which may occur at the time of insertion of the stent into the site to be applied since the tops of the arched elements are prevented from curvature deformation when expanding the stent and minimized in curvature deformation which may occur at the time of bending of the stent. Further, the stent is scarcely changed in length at the time of expansion thereof since the ratio between the distance from the radially halving line of the annular member to the top of the arched segment that connects the second linear segment and third linear segment of the first annular member element and the distance from the radially halving line of the annular member to the top of the arched segment that connects the first linear segment and second linear segment of the second annular member element is set to 7:8.

Embodiment 3

Figure 7:
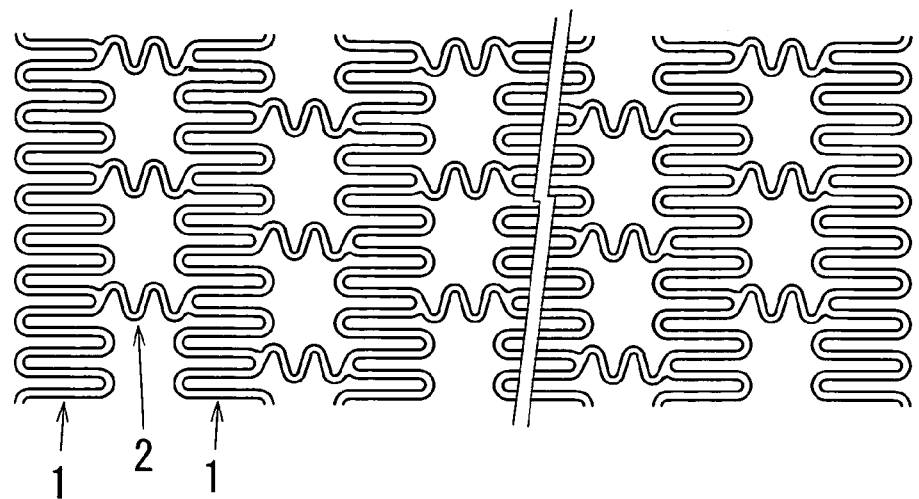
FIG. 7 is a development of a stent according to another embodiment of the present invention.

Embodiment 3 of the present invention will be demonstrated below, making reference to FIG. 7.

The stent of embodiment 3 is a modification of the stent of embodiment 1, in which the connecting elements 2 are formed into a shape as shown in FIG. 5D. As shown in FIG. 7, the stent comprises ten annular members 1 which are radially expandable and arranged in the direction of the longitudinal axis of the stent, the adjoining annular members 1, 1 are connected to each other by three wavelike connecting elements 2 shown in FIG. 5D. The aforementioned stent is excellent in trackability to lumens since the whole stent is flexible enough to respond to bending. Further, it is easy to provide the stent with a lateral hole. In addition, the tops of the arched elements are prevented from producing curvature deformation when expanding the stent and minimized in curvature deformation which may occur at the time of bending of the stent, thus making it possible to avoid any damage of the blood vessels which may occur during insertion of the stent into the site to be applied. Further, the stent does not show change in length at the time of expansion.

Embodiment 4

Figure 8:
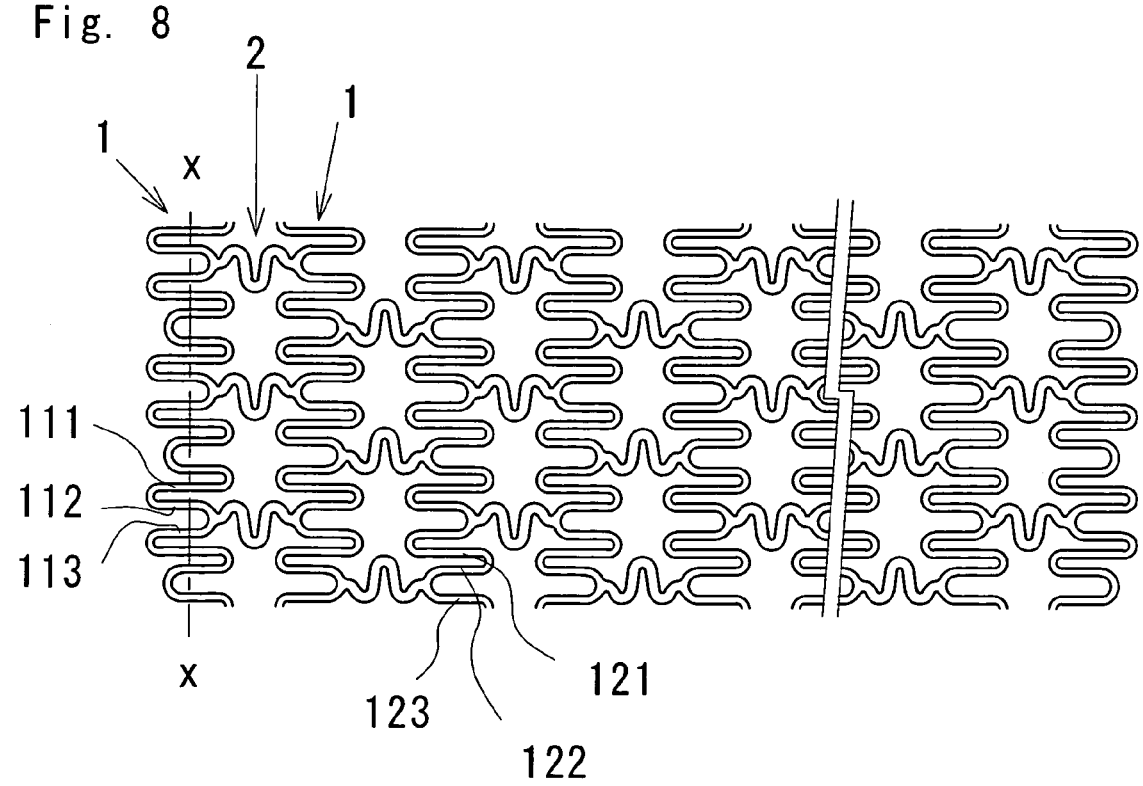
FIG. 8 is a development of a stent according to another embodiment of the present invention.

Embodiment 4 of the present invention will be demonstrated below, making reference to FIG. 8.

The stent of embodiment 4 is a modification of the stent of embodiment 1, in which ratio of the distances from the radially halving line X to the respective tops of the arched segments is set to 3:5, and the distance between the second linear segment 112(122) and the third linear segment 113(123) is set to two times of the distance between first linear segment 111(121), second linear segment 112(122), and the connecting elements 2 are formed into a shape as shown in FIG. 5C. As shown in FIG. 8, the stent comprises fourteen annular members 1 which are radially expandable and arranged in the longitudinal direction thereof, and the adjoining annular members 1, 1 are connected to each other by three connecting elements 2 with a shape as shown in FIG. 5C.

The aforementioned stent is no less excellent in trackability to lumens than the stent demonstrated in embodiment 1 since the whole stent is flexible enough to respond to bending. Further, it is easy to provide the stent with a lateral hole. In addition, the tops of the arched elements are prevented from producing curvature deformation when expanding the stent and minimized in curvature deformation which may occur at the time of bending of the stent, thus making it possible to avoid damages of the blood vessels which may occur when introducing the stent into the site to be applied. Further, the stent does not show change in length at the time of expansion, In this embodiment, the ratio of distances from the radially halving line of the annular member to the tops of respective arched segment is set to 3:5, but the stent is scarcely changed in length at the time of expansion because of the fact that the distance between the second linear segment and third linear segment is set to two times as large as the distance between the first linear segment and second linear segment.

Embodiment 5

Figure 9:
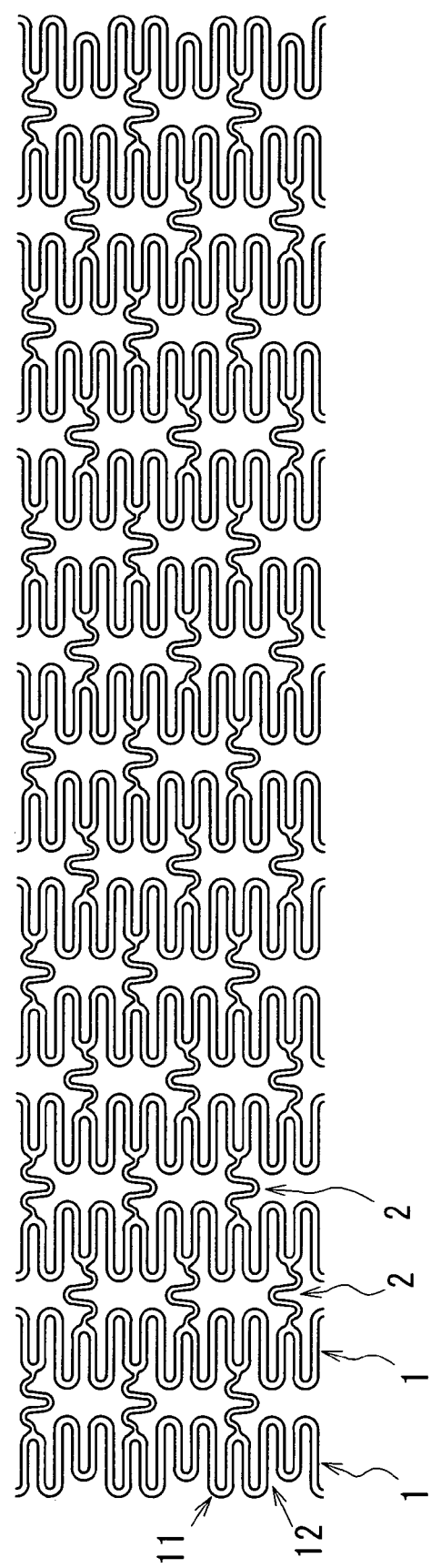
FIG. 9 is a development of a stent according to another embodiment of the present invention.

Embodiment 5 of the present invention will be demonstrated below, making reference to FIG. 9.

The stent of embodiment 5 is a modification of the stent of embodiment 1, in which the ratio of distances from the radially halving line to the respective tops of the arched segments is set to 3:5, and the connecting elements 2 are formed into a shape as shown in FIG. 5C. As shown in FIG. 9, the stent comprises fourteen annular members 1 which are radially expandable and arranged in the longitudinal direction thereof, and the adjoining annular members 1, 1 are connected to each other by three connecting elements 2 with a shape as shown in FIG. 5C.

The aforementioned stent is no less excellent in trackability to lumens than the stent demonstrated in embodiment 1 since the whole stent is flexible enough to respond to bending. Further, it is easy to provide the stent with a lateral hole. In addition, the tops of the arched elements are prevented from curvature deformation when expanding the stent and minimized in curvature deformation which may occur at the time of bending of the stent, thus making it possible to avoid damages of the blood vessels which may occur during insertion of the stent into the site to be applied. However, the stent may be shortened at the time of expansion because of the fact that the ratio of distances from the radially halving line of the annular member to the top of each arched segment is set to 3:5.

Embodiment 6

Figure 10:
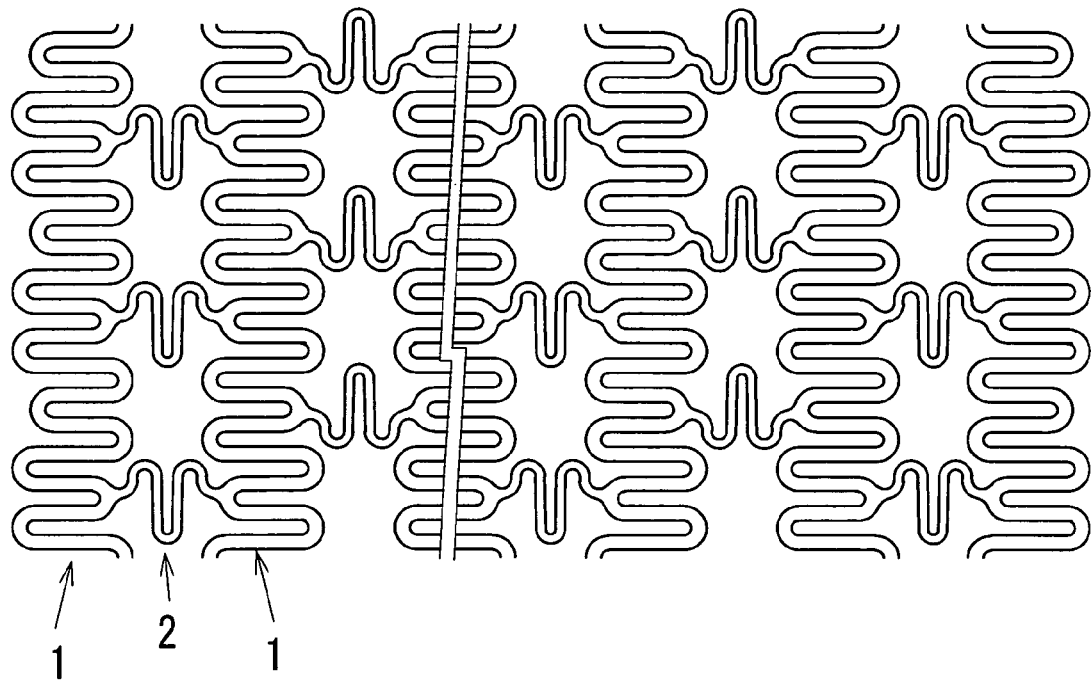
FIG. 10 is a development of a stent according to another embodiment of the present invention.

Embodiment 6 of the present invention will be demonstrated below, making reference to FIG. 10.

The stent of embodiment 6 is a modification of the stent of embodiment 1, in which the amplitude of the wavelike elements 11, 12 is set to $6/7$, and the connecting elements 2 is formed into a waveform as shown in FIG. 5B. As illustrated in FIG. 10, the stent comprises twelve annular members 1 which are radially expandable and arranged in the longitudinal direction thereof, and the adjoining annular members 1, 1 are connected to each other by three connecting elements 2 with a shape as shown in FIG. 5B. The present stent is excellent in trackability to lumens since the whole stent is flexible enough to respond to bending as well as the stent demonstrated in embodiment 1. Further, it is easy to provide the stent with a lateral hole. In addition, the tops of the arched elements are prevented from curvature deformation when expanding the stent and minimized in curvature deformation which may occur at the time of bending of the stent, thus making it is possible to avoid damages of the blood vessels when introducing the stent into the site to be applied. Further, the length of the stent is scarcely varied at the time of expansion thereof.

Embodiment 7

Figure 11:
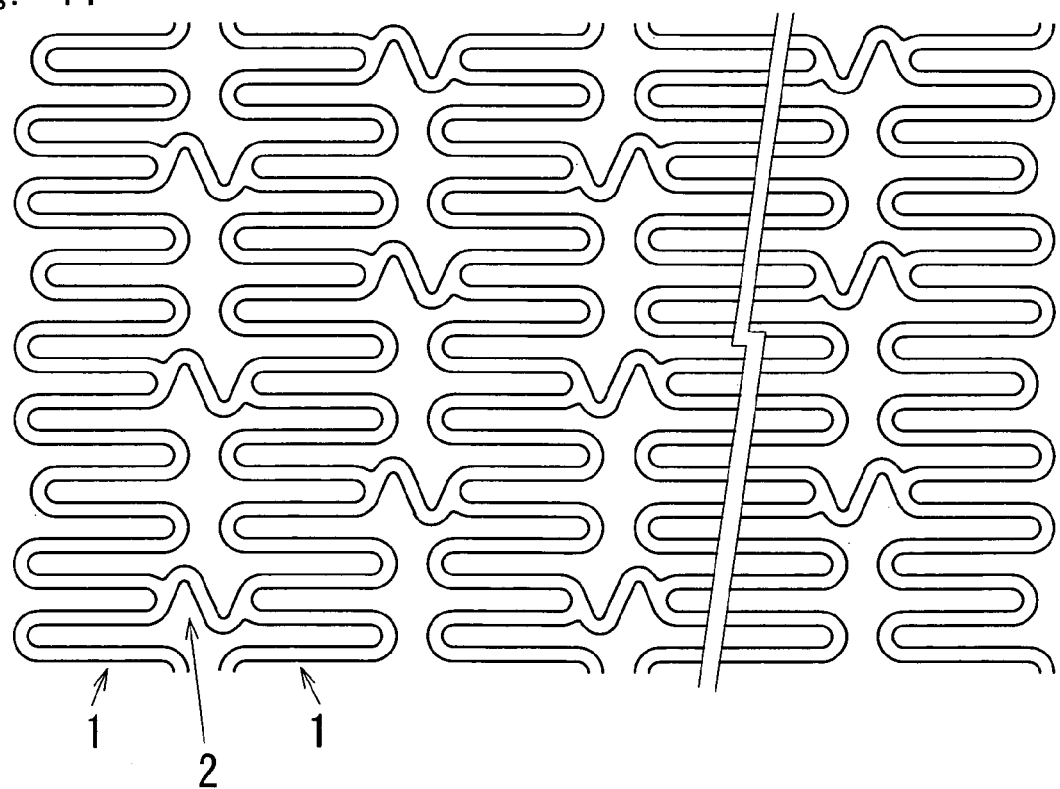
FIG. 11 is a development of a stent according to another embodiment of the present invention.

Embodiment 7 of the present invention will be demonstrated below, making reference to FIG. 11.

A stent of embodiment 7 is a modified form of embodiment 1, in which the connecting elements 2 are of S-shaped form as shown in FIG. 5A. As illustrated in FIG. 11, the stent comprises thirteen annular members 1 which are radially expandable and arranged in the longitudinal direction thereof, and the adjoining annular members 1, 1 are connected to each other by S-shaped three connecting elements 2 as shown in FIG. 5A. The whole stent is flexible enough to respond to bending as well as the stent demonstrated in embodiment 1, so that the stent of the present embodiment is excellent in trackability to lumens. Further, it is easy to provide the stent with a lateral hole. In addition, the tops of the arched elements are prevented from curvature deformation when expanding the stent and minimized in curvature deformation which may occur at the time of bending of the stent, thus making it is possible to avoid damages of the blood vessels when introducing the stent into the site to be applied. Further, the length of the stent is scarcely varied at the time of expansion thereof.

Embodiment 8

Figure 12:
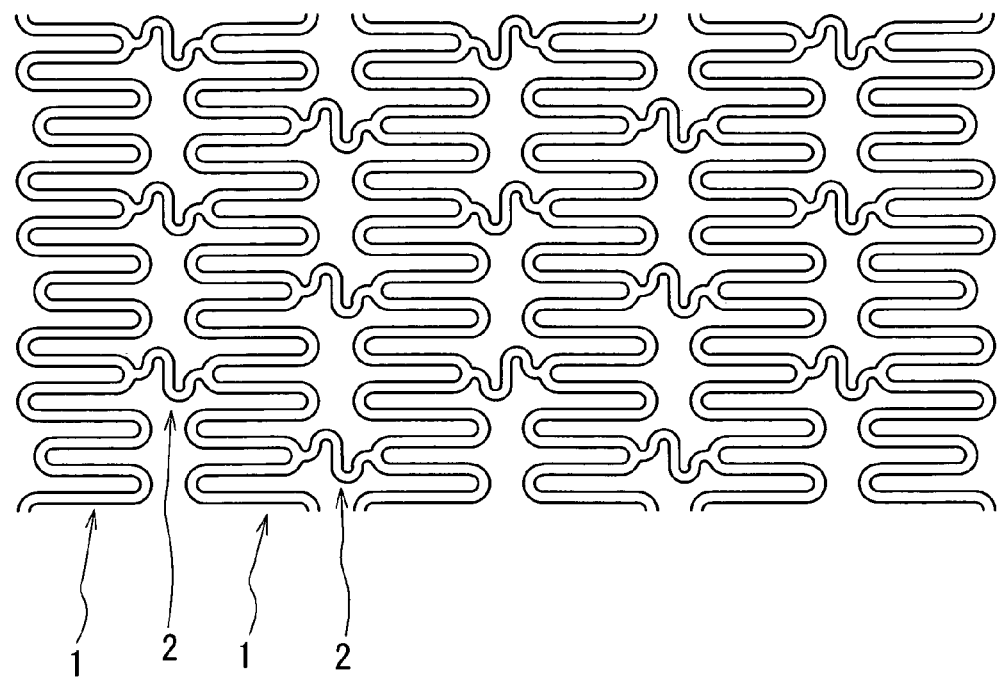
FIG. 12 is a development of a stent according to another embodiment of the present invention.

Embodiment 8 of the present invention will be demonstrated below, making reference to FIG. 12.

Figure 5F:
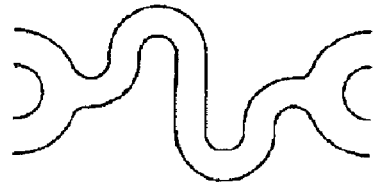

A stent of embodiment 8 is a modified form of embodiment 1, in which the ratio of distances from the radially halving line to the respective tops of the arched segments is set to 3:4, and the connecting elements 2 are made into a shape as shown in FIG. 5F. As illustrated in FIG. 12, the stent comprises six annular members 1 which are radially expandable and arranged in the longitudinal direction thereof, and the adjoining annular members 1, 1 are connected to each other by three connecting elements 2 with a shape as shown in FIG. 5F. The stent of the present embodiment is excellent in trackability to lumens since the whole stent is flexible enough to respond to bending as well as the stent demonstrated in embodiment 1. Further, it is easy to provide the stent with a lateral hole. In addition, the tops of the arched elements are prevented from curvature deformation when expanding the stent and minimized in curvature deformation which may occur at the time of bending of the stent, thus making it is possible to avoid damages of the blood vessels when introducing the stent into the site to be applied. Further, the length of the stent is scarcely varied at the time of expansion thereof.

Embodiment 9

Figure 13:
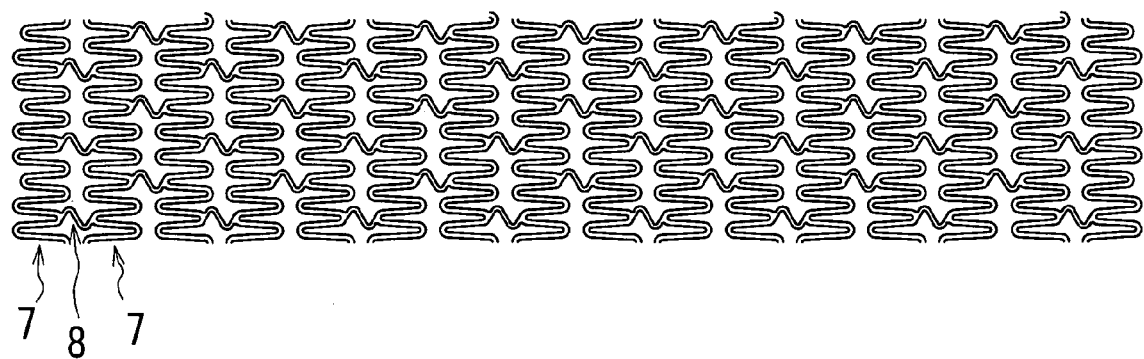
FIG. 13 is a development of a stent according to an embodiment of the present invention (second invention)
Figure 14:
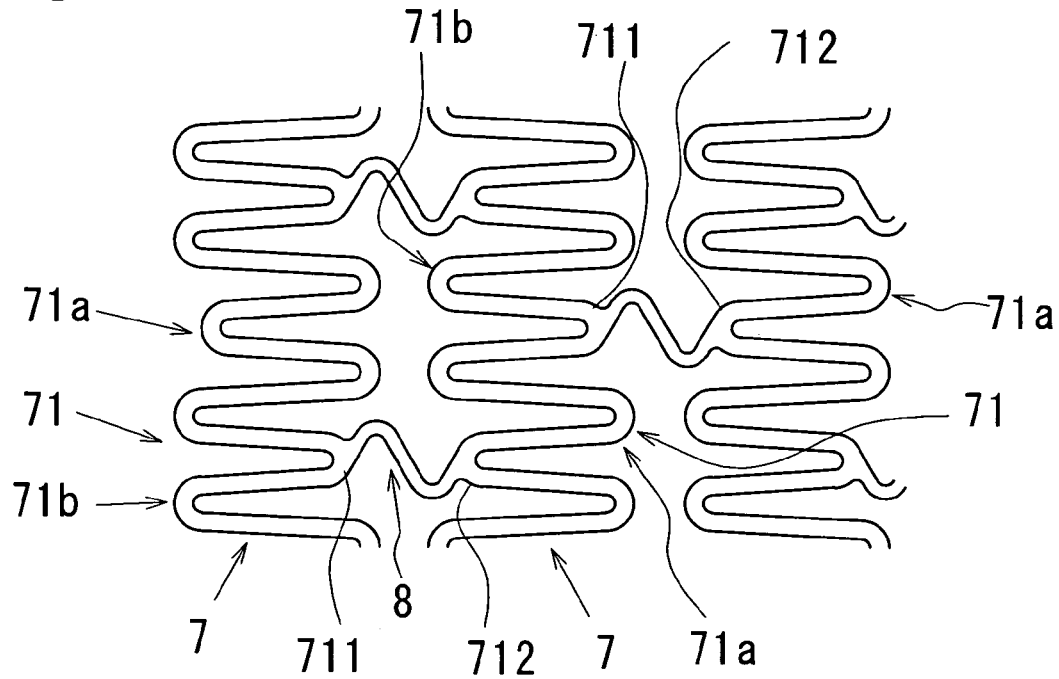
FIG. 14 is a partially enlarged view of FIG. 13.

FIG. 13 is a development of a stent illustrating another embodiment of the present invention (second invention), and FIG. 14 is a partially enlarged view of the stent shown in FIG. 13.

The stent of the present invention comprises, as illustrated in FIGS. 13 and 14, thirteen annular members 7 which are radially expandable and arranged in the longitudinal direction thereof. The adjoining two annular members 7, 7 are joined together in the longitudinal direction thereof by three connecting elements 8. The annular members 7 are composed of circumferentially connected wavelike elements 7 of an M-shaped waveform, and arranged in the longitudinal direction thereof. The individual wave portion that constitutes the wavelike element 7 is in the form of a substantially sinusoidal wave. The adjoining two annular members 7, 7 are joined together through the connecting elements 8 by connecting tops 711 of the mountains of the trough elements 71b in the wavelike elements 71 of one annular member 7 and bottoms 712 of the trough of the mountain elements 71a in the wavelike elements 71 of the other annular member 7.

The annular member 7 is a part constituting a luminal wall of the stent and is a radially expandable portion for holding a luminal diameter of the blood vessel after placement of the stent in the blood vessel. The annular members 7 are respectively composed of six wavelike elements 71 having an M-shaped waveform and being circumferentially connected. The annular members 7 are arranged in the longitudinal direction of the stent. As illustrated in FIG. 10, the wavelike element 71 comprises mountain elements 71a and trough elements 71b, each of which has an M-shaped waveform including one trough (one mountain) between two mountains (two troughs). The mountain element 71a is provided with a trough having a bottom 712 between two mountains, while the trough element 71b is provided with a mountain having a top 711 between two troughs.

In order to improve the expandability of the stent under the same wavelength, it is preferred to increase the amplitude of waveform of the wavelike elements 71. The stent is lengthened at the time of expansion thereof if the mountain (trough) having the top 711 (bottom 712) in the middle of the trough element 71b (mountain element 71a) is protruded on the side of the trough element 71b (mountain element 71a) of the wavelike element 71. Thus, it is preferred that the mountain (trough) having the top 711 (bottom 712) is protruded on the side of the mountain element 71a (trough element 71b) of the wavelike element 71. The protruded length of the mountain (trough) having the top 711 (bottom 712) is ⅘ of the height of the mountain element 71a (depth of the trough element 71b) of the wavelike element 71. The adjoining two annular members 7, 7 are out of phase with each other by a half wavelength of the wavelike element and are connected by the connecting elements 2 in the same longitudinal straight lines.

The adjoining two annular members 7, 7 are connected between the top 711 and bottom 712 closest to each other. As illustrated in FIG. 14, the tops 711 of the mountains of the trough elements 71b among the wavelike elements 71 of the annular member 7 on the proximal side are connected to the bottoms 712 of the troughs of the mountain elements 71a among the wavelike elements 71 of the annular member 7 on the distal side by the connecting elements 8.

The connecting elements 8 are made into a curved shape (waveform) as illustrated in FIG. 5F, and three connecting elements 8 are respectively provided between adjoining two annular members 7, 7. Further, the tops of the wave patterns of the wavelike elements 71 are formed to have a smooth contour.

Figure 15:
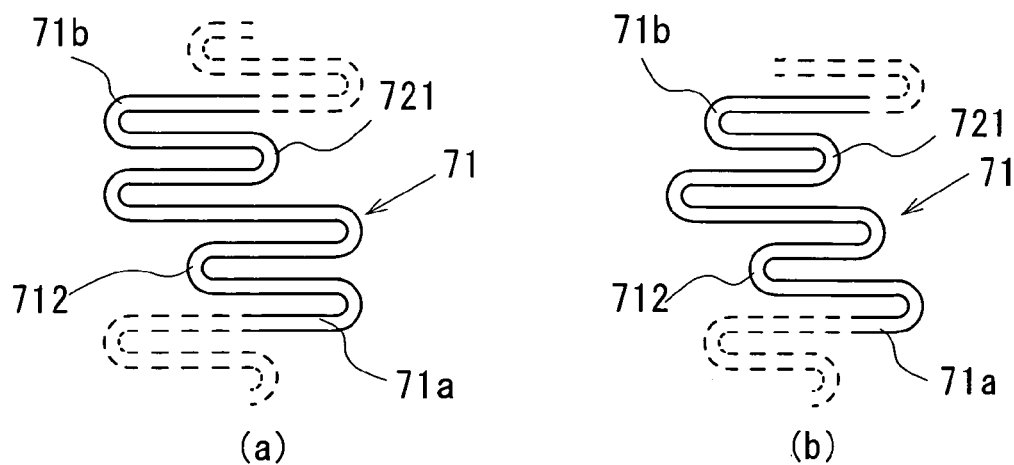
FIG. 15 is a partially enlarged view illustrating a modification of the stent of FIG. 13.

In FIG. 14, the right side of the drawing is set as the distal end of the stent for the sake of convenience. Further, the term "mountain" denotes the section of the wave that is convex rightward, while the term "trough" denotes the section of the wave that is convex leftward. Further, the wording "wavelike element with an M-shaped waveform" is a wavelike element composed of a combination of a mountain element having one trough between two mountains (M-shaped) and a trough element having one mountain between two troughs (reversed M-shaped). It is to be noted that the wavelike element is never limited to any wavelike element with a specific waveform, provided that it has one trough (one mountain) between two mountains (two troughs). It is possible to use any wavelike elements with various waveforms such as, for example, wavelike elements of which two mountains (two troughs) have the same wave height as illustrated in FIG. 15a, or wavelike elements of which two mountains (two troughs) have different wave heights as illustrated in FIG. 15b. Although four linear segments (ridgelines of the mountains or troughs) that constitute the M-shaped element are substantially in the form of a sinusoidal waveform, these segments are not necessarily required to have such a substantially sinusoidal waveform. They may be in the form of a straight line or parallel line.

In the above embodiment, the linear segment including a point that connects the M-shaped element and the reversed M-shaped element (that corresponds to the first linear segment of the first annular member element or second annular member element in Embodiment 1) has a length longer than that of two linear segments that constitute the trough or mountains. However, the two linear segments that constitute the trough or mountain (that correspond to the second linear segment and third linear segment of the first annular member element or second annular member element in Embodiment 1) are not necessarily required to have the same length, the linear segment in the middle position (that corresponds to the second linear segment) may have a length shorter than the linear segment in the lower position (that corresponds to the third linear segment). The stent of the above embodiment is excellent in trackability to lumens since the whole stent is flexible enough to respond to bending for the reasons that the annular members constituting the luminal wall of the stent in the above embodiment comprise plural wavelike elements having an M-shaped form. Further, it is easy to provide the stent with a lateral hole.

The stent is apt to slightly shorten the length after expansion for the reasons that the annular members are connected between the top of the mountain located in the middle of the trough element of the wavelike elements of one annular member and the bottom of the trough positioned in the middle of the mountain elements of the wavelike elements of the other annular member by the connecting element, and that the protruded length of the mountain (trough) in the wavelike element is ⅘ of the height of the mountain (depth of the trough) of the wavelike element. Further, the adjoining two annular members are joined together at the middle of the M-shaped element, so that the stent causes no curvature deformation at the top of the mountain when expanding the stent. Further, it is possible to minimize damages of the blood vessel when guiding the stent to the site to be applied since the whole M-shaped element produces little warpage.

[Flexibility, Shortening and Vessel Diameter Holding Capacity Tests]

Figure 16:
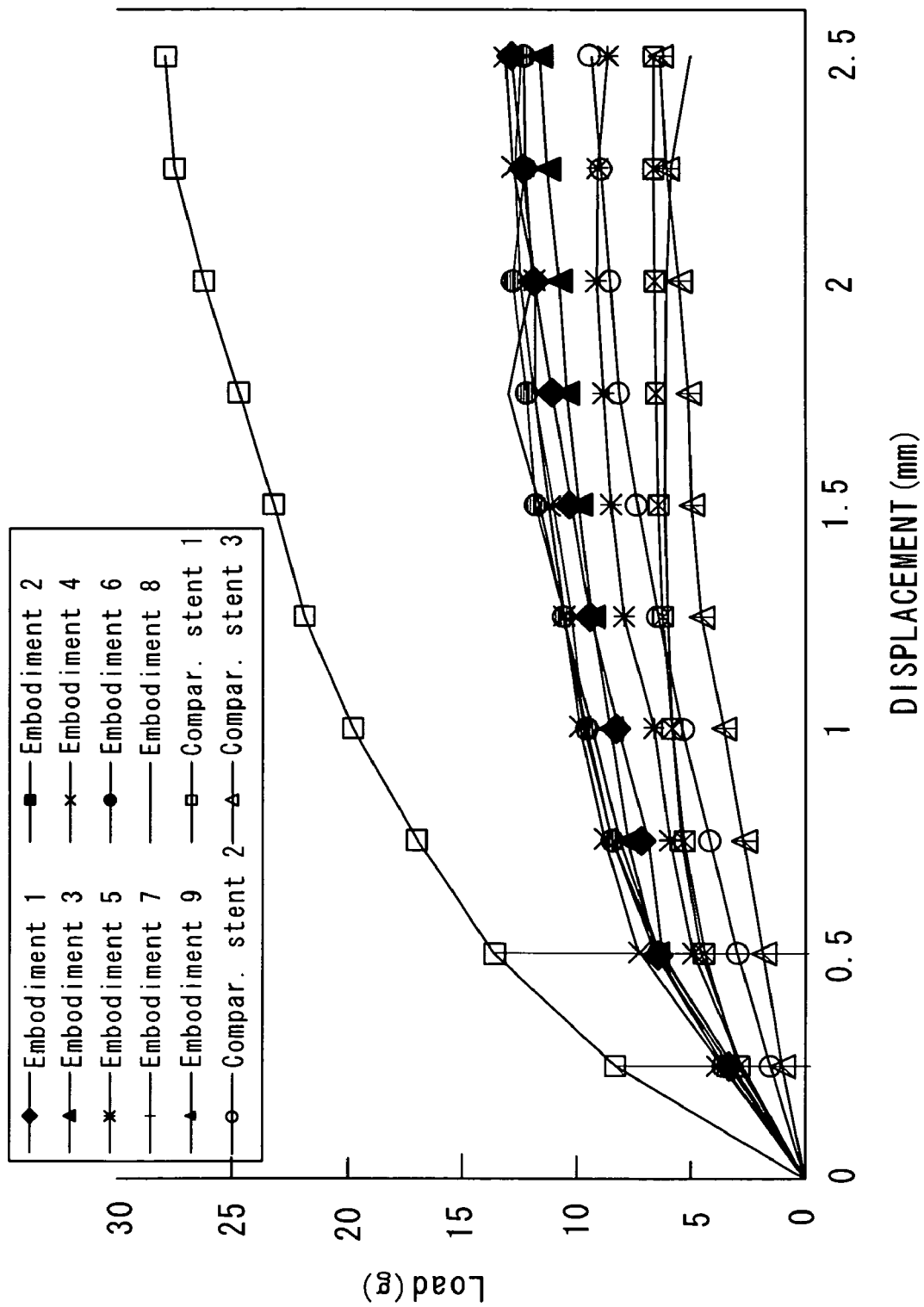
FIG. 16 is a graph for making a comparison between the flexibility of the stent of the present invention and that of the prior art.
Figure 17:
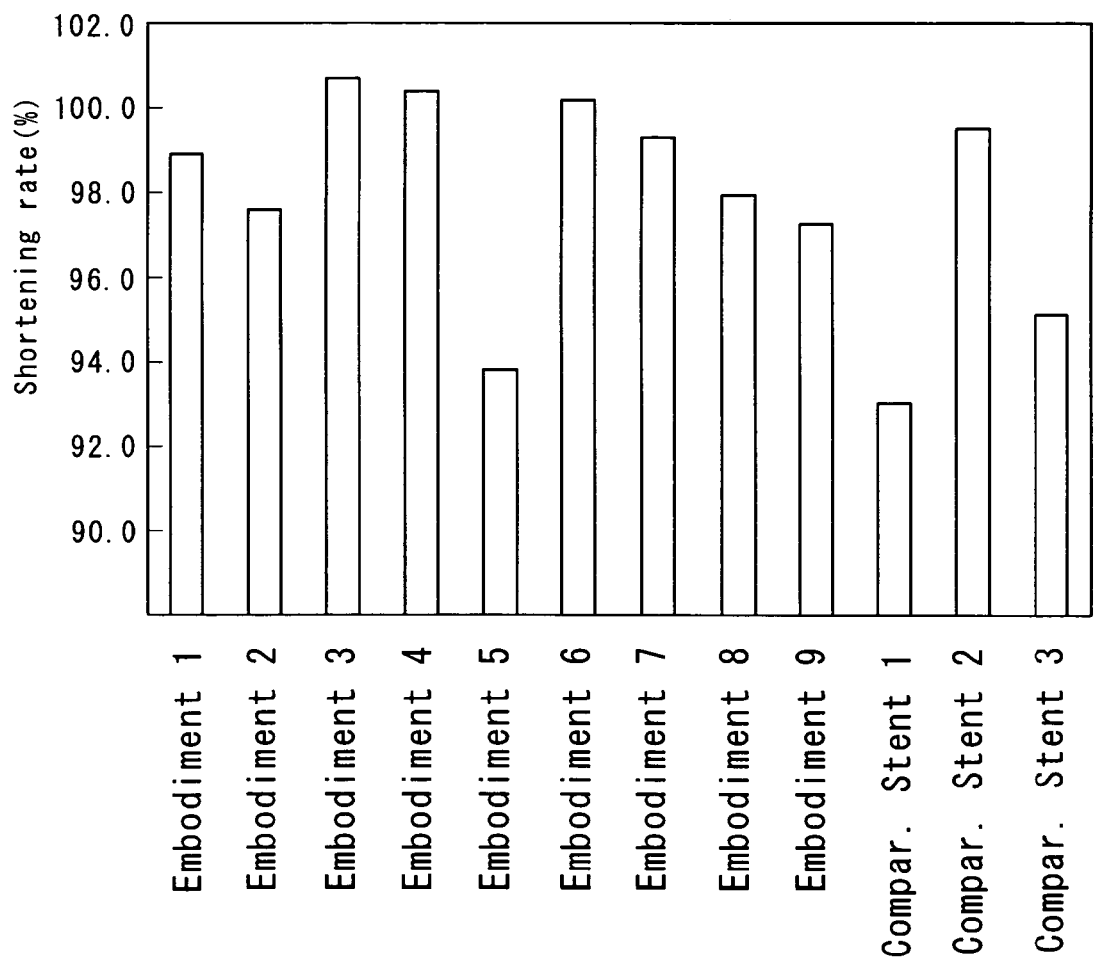
FIG. 17 is a graph for making a comparison in shortening between the stent of the present invention and that of the prior art.
Figure 18:
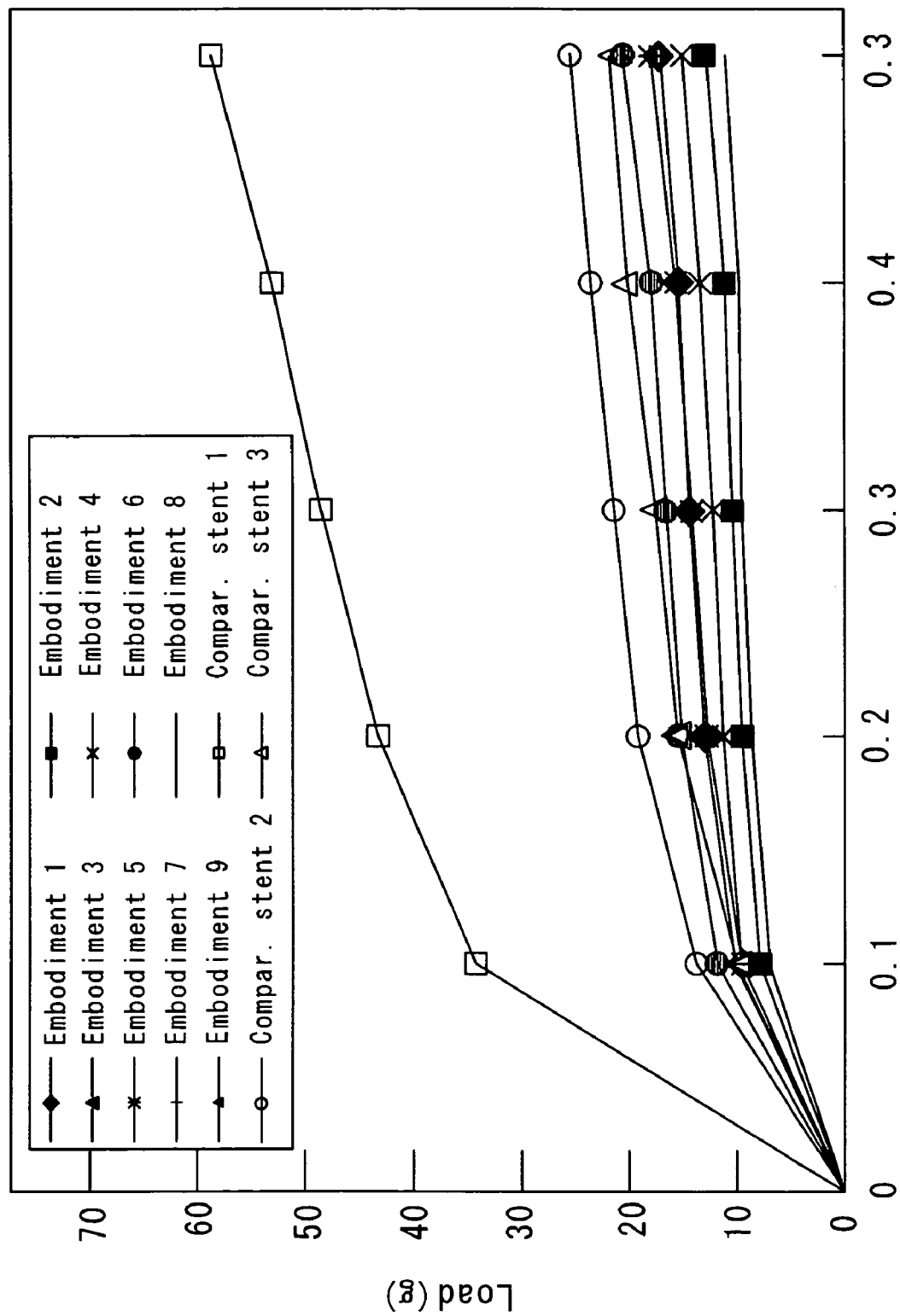
FIG. 18 is a graph for making a comparison in vessel holding capacity between the stent of the present invention and that of the prior art.

FIGS. 16-18 show comparison results relating to flexibility (bendability), shortening and vessel diameter holding capacity of the stents having developments as shown in Table 1.

From the results shown in FIG. 16, the stent of the present invention is substantially equal to the stent of the prior art in flexibility. From the results shown in FIG. 17, the stent of the present invention is superior in shortening to the stent of the prior art. Further, it will be understood that the shortening due to expansion of the stent can be prevented by appropriate selection of the ratio of distances from the radially halving line X to the respective tops of the arched segments. From the results shown in FIG. 18, the stent of the present invention is substantially equal to the stent of the prior art in vessel diameter-holding capacity.

For the flexibility, measurement was made by fixing the stent at one end and pushing a part of the stent 5 mm remote from the fixed end to bend the stent, and measuring a load which corresponds to the displacement magnitude.

The measurement of shortening was carried out by using a balloon of a 3.0 mm diameter to expand the stent at a pressure of 8 atm. (for the reference stent, at the recommended pressure) for 30 seconds, and a profile projector (made by Mitutoyo Corporation) to determine the length of the expanded stent after expansion.

In order to determine the vessel diameter holding capacity, compression test was carried out with Autograph (made by Shimadzu Corporation) on the stent expanded by pressurizing the stent at 8 atm. (for the reference stent, at the recommended pressure) for 30 seconds with a balloon of a 3.0 mm diameter. The resultant data were divided by the number of the annular members to determine the result as the vessel diameter holding capacity.

TABLE 1

| | Remarks |
|---|---|
| Embodiment 1 | FIG. 2(ratio of distances from the radially halving line to the respective tops of the arched segments is 4:5, shape of the connecting element: FIG. 5B) |
| Embodiment 2 | FIG. 6(ratio of distances from the radially halving line to the respective tops of the arched segments is 7:8, shape of the connecting element: FIG. 5E, the tops of the arched segments at both ends of the stent are aligned with each other.) |
| Embodiment 3 | FIG. 7(ratio of distances from the radially halving line to the respective tops of the arched segments is 4:5, the shape of the connecting element: FIG. 5D) |
| Embodiment 4 | FIG. 8(ratio of distances from the radially halving line to the respective tops of the arched segments is 3:5, the shape of the connecting element: FIG. 5C, the distance between second linear segment and third linear segment is twice the distance between first linear segment and second linear segment) |
| Embodiment 5 | FIG. 9(ratio of distances from the radially halving line to the respective tops of the arched segments is 3:5, shape of the connecting element: FIG. 5C) |
| Embodiment 6 | FIG. 10(ratio of distances from the radially halving line to the respective tops of the arched segments is 4:5, shape of the connecting element: FIG. 5B, amplitude of wavelike element is 6/7 of that in embodiment 1) |
| Embodiment 7 | FIG. 11(ratio of distances from the radially halving line to the respective tops of the arched segments is 4:5, shape of the connecting element: FIG. 5A) |
| Embodiment 8 | FIG. 12(ratio of distances from the radially halving line |

TABLE 1-continued

Figure 19:
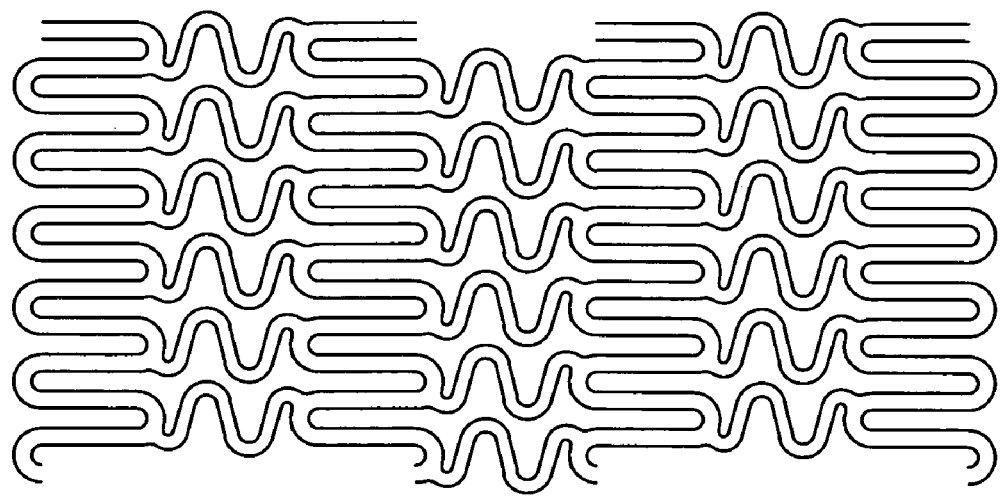
FIG. 19 is a development of a stent of the prior art.
Figure 20:
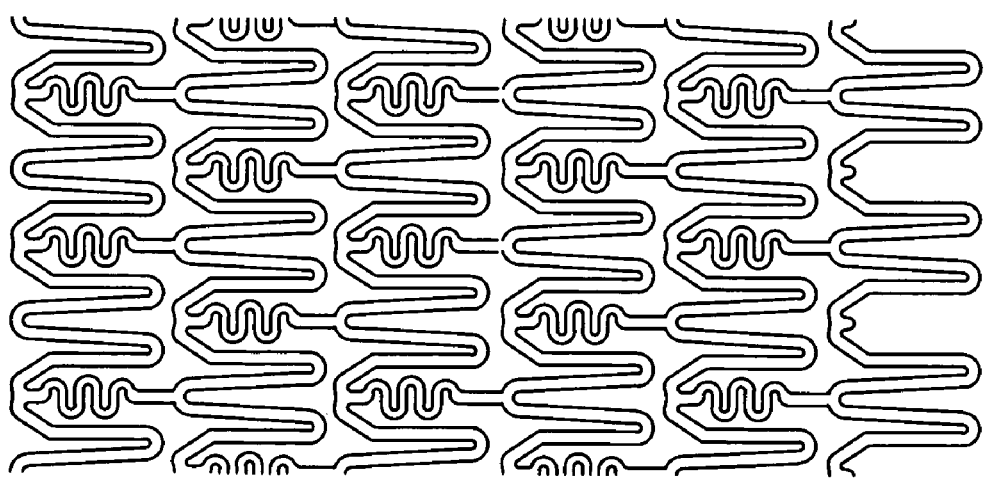
FIG. 20 is a development of a stent of the prior art.
Figure 21:
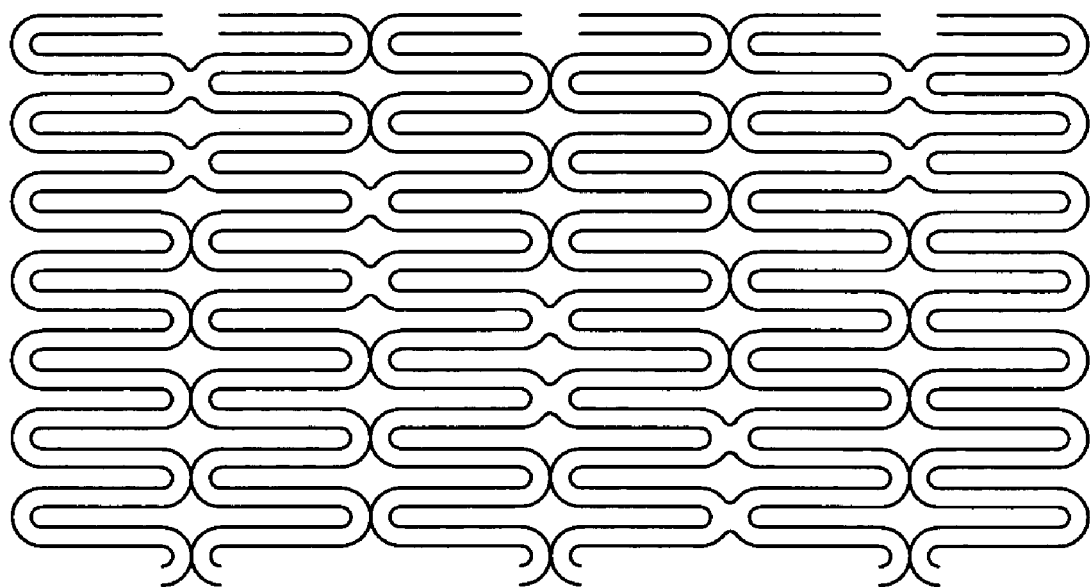
FIG. 21 is a development of a stent of the prior art.

| | Remarks |
|---|---|
| | to the respective tops of the arched segments is 3:4, shape of the connecting element: FIG. 5F) |
| Embodiment 9 | FIG. 13(Protruded length of the mountain in the middle of the trough is 4/5 of the mountain height of the wavelike element, shape of respective waves that constitute wavelike element: sinusoidal waveform, shape of the connecting element: FIG. 5A) |
| Comparative stent 1 | FIG. 19(blood vessel-retaining portion with a wavelike pattern and joint elements with a waved form) |
| Comparative stent 2 | FIG. 20(blood vessel-retaining portions with a wavelike pattern are connected to each other at the tops and bottoms of the waves) |
| Comparative stent 3 | FIG. 21(blood vessel-retaining portions with a wavelike pattern are connected to each other at the tops and bottoms of the waves) |

The invention claimed is:

1. An expandable flexible stent for use in blood vessels, comprising:

a plurality of radially expandable annular members aligned one after another in a longitudinal direction, and one or more connecting elements located between said annular members adjacent to each other in the longitudinal direction of the stent to connect them, wherein each of said annular members comprises first annular member elements and second annular member elements alternately connected with each other in a circumferential direction of the stent, wherein each of said first annular member elements in a development of the stent includes first, second and third linear segments which extend longitudinally and parallel to one another, said second linear segment and third linear segment being equal in length, while the first linear segment being different in length from said second and third linear segments, said first linear segment and said second linear segment being connected by an arched segment that is convex toward a proximal side of the stent, while said second linear segment and third linear segment being connected by an arched segment that is convex toward a distal side of the stent, wherein each of said second annular member elements in the development of the stent includes first, second and third linear segments which extend longitudinally and parallel to one another, said second linear segment and third linear segment of each second annular member element being equal in length, while said first linear segment of each second annular member element being different in length from said second and third linear segments of each second annular member element, said first linear segment and second linear segment of each second annular member element being connected by an arched segment that is convex toward the distal side of the stent, while said second linear segment and third linear segment of each second annular member element being connected by an arched segment that is convex toward the proximal side of the stent, wherein said first annular member elements and second annular member elements in each annular member are arranged alternately around a circumference of the stent, and are connected such that each of the second annular member elements is connected to the adjacent first annular member element on one side thereof by an arched segment that is convex toward the proximal side of the stent and located between the first linear segment of the second annular member element on the one side, and is connected to the adjacent first annular member element on an opposite side thereof by an arched segment that is convex toward the distal side of the stent and located between the third linear segment of the second annular member element and the first linear segment of the adjacent first annular member element on the opposite side thereof, wherein the annular members adjacent to each other in the longitudinal direction of the stent are connected by said one or more connecting elements, each of said one or more connecting elements being connected at one end thereof to the arched segment joining the second and third linear segments of the first annular member elements of the annular member located on the proximal side of the stent, and at the other end thereof to the arched segment joining the second and third linear segments of the adjacent annular member on the distal side of the stent, wherein the arched segments at opposite ends of each of the connecting elements are arranged along the same straight line extending in a direction parallel to the longitudinal axis of the stent.

2. The stent according to claim 1, wherein each of the first linear segments of the first and second annular member elements is longer than said second linear segment and third linear segment on a respective annular member element.

3. The stent according to claim 1, wherein a ratio of a distance from a radially halving line of each of the annular members to the top of the arched segment that connects the second linear segment and the third linear segment of the first annular member element, to a distance from the radially halving line of the annular member to the top of the arched segment that connects the first linear segment and the second linear segment of the second annular member element is in the range of 1:2 to 7:8.

4. The stent according to claim 1, wherein each of the annular members is out of phase with the adjacent annular member in the longitudinal direction.

5. The stent according to claim 1, wherein each of the annular members is out of phase with the adjacent annular member in the longitudinal direction by a half wavelength.

6. The stent according to claim 1, wherein each of the connecting elements is in the form of an arc-shaped line which follows the circumference of the stent.

7. The stent according to claim 1, wherein each of the connecting elements is in the form of a pair of arc-shaped lines which are parallel to each other and which follow the circumference of the stent.

8. The stent according to claim 7, wherein each of the connecting elements is in the form of a wavelike shape and has a mountain.

9. The stent according to claim 7, wherein each of the connecting elements is in the form of a wavelike shape and has plural mountains.

10. The stent according to claim 1, wherein two to six of the connecting elements are provided at even intervals between convex sides of the arched segment of each of said adjacent annular members.

11. The stent according to claim 1, wherein the arched segments of the annular members situated, respectively, at each end of the stent are respectively aligned along a proximal or distal end of the stent.

12. The stent according to claim 1, wherein the linear segments of each of the first annular member elements and each of the second annular member elements are arranged circumferentially at even intervals.

13. The stent according to claim 1, wherein for each of the first and second annular member elements, a distance between said first linear segment and second linear segment is equal to a distance between said third linear segment and first linear segment, and a distance between said second linear segment and third linear segment is greater than the distance between said first linear segment and second linear segment.

* * * * *

UNITED STATES PATENT AND TRADEMARK OFFICE
CERTIFICATE OF CORRECTION

PATENT NO. : 7,648,526 B2 Page 1 of 1
APPLICATION NO. : 10/554725
DATED : January 19, 2010
INVENTOR(S) : Sano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1100 days.

Signed and Sealed this

Twenty-eighth Day of December, 2010

David J. Kappos
*Director of the United States Patent and Trademark Office*